(12) United States Patent
Giuliani et al.

(10) Patent No.: US 8,178,136 B2
(45) Date of Patent: May 15, 2012

(54) **COMPOSITION BASED ON VEGETAL EXTRACTS OF *AJUGA REPTANS* FOR PREVENTING HAIR LOSS, STIMULATING THE GROWTH OF HAIR, REGULATING THE PRODUCTION OF SEBUM**

(75) Inventors: Giammaria Giuliani, Milan (IT); Anna Benedusi, Milan (IT); Salvatore Bellinvia, Pordenone (IT)

(73) Assignee: Giuliani S.p.A., Milan (IT)

( * ) Notice: Subject to any disclaimer, the term of this patent is extended or adjusted under 35 U.S.C. 154(b) by 84 days.

(21) Appl. No.: 12/803,113

(22) Filed: Jun. 18, 2010

(65) Prior Publication Data

US 2011/0020476 A1 Jan. 27, 2011

Related U.S. Application Data

(62) Division of application No. 11/667,644, filed on May 11, 2007, now abandoned.

(30) Foreign Application Priority Data

Mar. 24, 2005 (IT) .............................. MI2005A0498

(51) Int. Cl.
*A01N 65/00* (2009.01)
(52) U.S. Cl. ....................................................... 424/725
(58) Field of Classification Search ........................ None
See application file for complete search history.

(56) References Cited

FOREIGN PATENT DOCUMENTS
WO   WO 2004/033673   *   4/2004
* cited by examiner

*Primary Examiner* — Michael Meller
(74) *Attorney, Agent, or Firm* — Hedman & Costigan, P.C.; James V. Costigan

(57) ABSTRACT

The present invention relates to preparations based on vegetal extracts of *Ajuga reptans* for favouring the growth of hair and stimulating the hair bulb. The preparations of the invention are in suitable formulations for oral administration or local application and are specifically suitable for the prevention and treatment of androgenic alopecia in males and females.

3 Claims, 2 Drawing Sheets

COMPOSITION BASED ON VEGETAL EXTRACTS OF *AJUGA REPTANS* FOR PREVENTING HAIR LOSS, STIMULATING THE GROWTH OF HAIR, REGULATING THE PRODUCTION OF SEBUM

This application is a divisional application of Ser. No. 11/667,644, filed May 11, 2007 now abandoned which claims priority from PCT/EP2006/002745, filed Mar. 21, 2006 which claims the priority of Italian application Serial No. MI2005A000498, filed Mar. 24, 2005.

The present invention relates to a composition based on vegetal extracts of *Ajuga reptans* for stimulating hair growth.

In particular, the present invention relates to preparations based on vegetal extracts of *Ajuga reptans* for the prevention and treatment of androgenetic alopecia.

It is known that hair and hairs are keratinized filaments of an epidermic derivation characteristic of all mammals including human beings.

The life and growth of hair and hairs in mammals is regulated by the proliferation cycle of the keratinocytes present in the bulb matrix, whereas the pigmentation of hair derives from the presence of melanocytes between the cells of the matrix. Although hair growth is relatively rapid in mammals, from 0.1 to 0.4 mm per day in human beings, it is not unlimited. With the exception of a few specific cases in which it can continue for several years, its duration is generally short, typically from 2 to 5 months.

In the active growth phase (Anagen), the cells of the matrix in rapid proliferation produce new piliferous material. The Anagen phase is in turn divided into six steps in relation to the maturity of the bulb, papilla and hair growth. The longest growth phase is Anagen VI. On an average, 86% of the hair on the human scalp is in Anagen for an estimated period of 4 to 8 years.

This is followed by a regression period of the matrix which loses direct contact with the dermic papilla interrupting the nourishment flow and oxygen necessary for the hair growth (Catagen) phase. In this phase both the hair bulb and the dermic papilla remain connected by means of a basal lamina and slowly migrate towards the surface of the skin. Approximately 1% of the hair on the scalp is in Catagen phase for a period of about two weeks. In the terminal phase of the hair cycle (Telogen) the hair bulb acquires a club-shaped form and is detached from the papilla which "regresses". The papilla and bulb continue to move towards the surface of the skin almost as far as the graft of the erector muscle of the hair. The hair strand can remain in this condition for a more or less long period of time, but can be easily pulled and fall out. Before falling a new bud of the hair follicle is differentiated, which gives rise to a new cycle. About 13% of the hair on a human scalp is in Telogen phase for about 3-4 months.

The type of hair produced by the follicle can change and depends on signals of the hormonal type present in the underlying derma, in particular steroid hormones coming from the gonads and in some cases from the adrenal capsules, such as testosterone. This hormone, or its more active metabolite, 5α dihydrotestosterone, during puberty, causes the appearance of secondary sexual characteristics such as hair growth in the region of the pubis, armpits and, in males, beard with a transformation of fleece hair to terminal hair. It has recently been found that in males affected by androgenetic alopecia or baldness, terminal hair is transformed into fleece hair.

It is well known that baldness or androgenetic alopecia is the type of baldness by which the majority of persons suffering from hair loss are affected. This affection consists of a progressive miniaturization and surfacing of the hair follicles.

There is a genetic predisposition towards androgenetic alopecia. What is most probably transmitted are the enzymes interested in the conversion and collection of androgenic hormones, i.e.: the two iso-enzymatic forms of 5α-reductase (type 1 and type 2), P 450 aromatasis and the cytosolic receptor of androgens.

In men with a predisposition for androgenetic alopecia, hair loss can begin at any moment after puberty, when the seric androgen levels are growing, consequently for the expression of androgenetic baldness both testosterone and 5α-reductase which is capable of converting testosterone to dihydrotestosterone, are necessary. In men DHT seems to be most important for androgenetic alopecia, whereas for women DHEA (dehydroepiandrosterone), produced by the adrenal glands to an extent of 95% and the androstenedione produced for 50% by the ovary and 30% by the adrenal glands. These hormones have a rather weak androgenic activity, on a peripheral level, however, there is a stronger amount converted to hormones with an androgenic activity.

DHT is harmful for genetically predisposed hair follicles of the scalp. It is this hormone which transforms fleece hair into terminal hair in adolescents. It has also been verified that other transformations of this hormone cause seborrhea. The 5α-reductase enzyme is abundant in the scalp for favouring the accumulation of DHT. Under the action of DHT, the hair follicles become increasingly smaller and consequently the hairs generated are also smaller and seem much less numerous. The production of pigment decreases, giving the impression of a lack of hair, even if this is present in a finer and pimentless form. The growth phase (anagen) also shortened and consequently the hair is less long.

An autoimmune reaction of the follicle complicates the situation, initiated and complicated by the DHT in which the immunitary system identifies the follicle damaged by the DHT as a foreign body and tries to eliminate it. Some forms of alopecia are characterized by the presence of inflammatory infiltrates in the perifollicular dermic regions. A study carried out on hair bulbs obtained from males affected by androgenetic alopecia showed, in the transition zones between areas with and without hair, the presence of mastocytary degranulation and leucocytary infiltration initially present in the bulge area, a presumed residence area of staminal cells of the hair system, with subsequent extension to the peribulbar region. The final result of the phlogistic process is a fibrotic and cicatricial transformation of the follicle with loss of the staminal cells and consequently of the hair regrowth capacity. After a few years, the follicles no longer produce terminal hair, but hair called "fleece", i.e. similar to that of newborn babies, not pigmented by the natural hair colour and extremely small, almost invisible.

What seems important is not the quantity of testosterone present in the blood but the concentrations, at a pilum-sebaceous level, of the enzymes necessary for converting the weaker androgens to stronger androgens and also the concentration of the androgen receptor.

Type 1 of 5α-reductase is the cutaneous type and is mainly localized in the sebaceous glands, in the liver, secondly in the keratinocytes of the skin and follicle, in the dermic papilla, in the sudoriparous glands. Type 2 of 5α-reductase is localized in the epididymus, seminal vesicles, prostate and cutis of fetus genitals, in the epithelial sheath of the hair follicles, in fibroblasts of the skin of genitals.

Known inhibitors of type 1 are: azelaic acid and its derivatives; inhibitors of type 2 are: finasteride and Ru5884, whereas inhibitors of both are: duasteride, copper and Revivogen (a mixture of natural substances among which pycnogenol).

Other inhibitors described in literature are: progesterone, zinc, gamma linoleic acid, betasitosterol, nettle, green tea, saw palmetto and some polyphenols.

Some of these vegetal substances, such as betasitosterol, produce their action by interacting with 5α-reductase substituting the testosterone, like other competitive inhibitors such as finasteride and duasteride.

Preparations based on active principles of a synthetic origin are currently used in the treatment and prevention of hair loss, such as, for example, minoxidil, or finasteride whose consumption often causes the formation of side-effects, which can also be quite significant.

Alternatively, preparations of a vegetal origin are on the market, whose consumption, although being free of side-effects, does not allow interesting results to be obtained, from an aesthetic point of view.

The present invention therefore derives from the necessity of finding preparations for stimulating the physiological trophism of hair bulbs whose administration does not have the disadvantages of the preparations of the known art.

The Applicant has found a selected herb from which it is possible to extract vegetal principles which can be applied for preventing and slowing down hair loss through a protective action on some of the components of the hair bulb.

This selected plant consists of *Ajuga reptans*, a species belonging to the Labiatae family, typical of the grassy areas of Europe, West Asia and Africa.

*Ajuga reptans* has been well-known as an officinal plant since ancient times, mainly for its use as an anti-rheumatic agent, tonic, astringent and as a light narcotic or antihemorrhagic and cicatrizing agent.

The antihemorrhagic effect has been experimentally demonstrated (Breschi et al, 1992) and attributed to a vasoconstrictive effect mediated by vasal α-adrenoreceptors. Antipyretic, antibacterial (Cantrell C L, 1999), anthelminthic (Kuria et al, 2002) and hypoglycemizing (Hilaly J E, Lyoussi B. 2002) activities are also known.

As *Ajuga* is also known for its "insect-repellant" properties, it has raised certain interest in the field of biological agriculture.

One of the general objectives of the present invention consists in supplying compositions based on vegetal extracts from a selected herb which are active in providing a stimulating action for hair growth.

Another objective of the present invention consists in supplying compositions based on vegetal extracts or active principles capable of preventing or treating androgenetic alopecia and telogenic defluvium.

A further objective consists in providing active principles of a vegetal nature which, when consumed orally or applied locally, provide a stimulating action on the hair bulb without causing significant side-effects in the subjects treated.

In view of the objectives specified above and according to a first aspect of the present invention, the use of an extract from *Ajuga reptans* is envisaged, for the production of a composition or preparation for stimulating hair growth, as specified in claim 1 enclosed.

Further characteristics and aspects of the invention are indicated in the subsequent claims.

Figure 1:
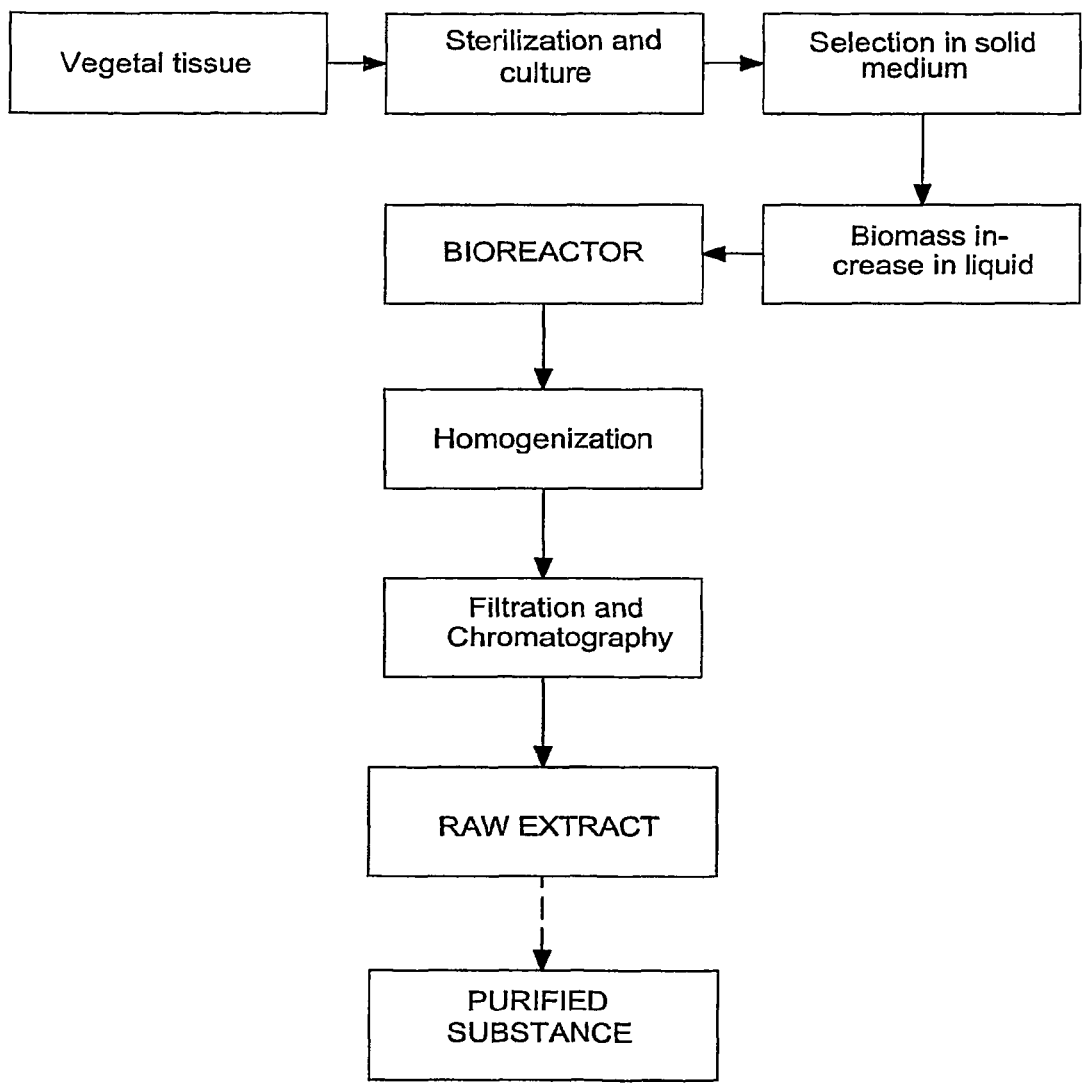
FIG. 1 is flow chart that illustrates the steps of the invention.

According to an embodiment of the invention the use of an extract from *Ajuga reptans* is provided for the production of a composition or preparation for the prevention or treatment of androgenetic alopecia and telogenic defluvium.

*Ajuga reptans* is a plant which produces a high quantity of compounds which can be attributed to various chemical groups. Among these are Iridoids, glycosilated monoterpene structures which form the bitter principles, such as arpagide and 8-O-acetyl-arpagide. In addition to iridoids, in the *Ajuga* species, antocyanes and two compounds belonging to the group of Flavonoids, Naringine neoesperidoside and Apigenine neoesperidoside.

In the leaves of *Ajuga reptans* compounds belonging to the group of ecdysones, pentacyclic triterpenes with a steroid structure, in particular beta-ecdysone and *Ajuga*-lactone, have also been characterized, to which an antifeedant activity with respect to insects has been ascribed. Other compounds with an analogous biological activity are derivatives of Clerodane, in particular 14,15-dihydroajugareptansine, 3α-hydroxyajugavensine B, 3β-hydroxyajugamarine F4 and ajugareptansine.

*Ajuga reptans* is also characterized by its capacity of producing Glycosilated Phenylpropanoids, hydrosoluble substances which belong to a very wide group of secondary metabolites commonly called phenylethanol glucosides. These are natural compounds soluble in water and widely distributed in the organs of upper plants.

From a structural point of view, they are characterized by the presence of a derivative of cinnamic acid and a derivative of phenylethanol, bound to the same molecule of beta-glucopyranose, one with an ester bond and the other with a glycoside bond. Other saccharide molecules, such as ramnose, xylose and apiose, are often bound to glucose which acts as a bridge between the two aromatic structures.

Phenylpropanoids are also classified as phenylpropanoid glucosides due to the presence in the molecule of a $C_6$-$C_3$ structure such as caffeic, ferulic or cinnamic acid, or as phenylethanoids for the contemporaneous presence of a derivative of phenylethanol or an analogous product. As the phenylethanol part, however, biosynthetically derives from a phenylpropanoic structure, it is currently preferable to define these structures as phenylpropanoids, but the various terms should be considered as being synonyms.

Acids bound to sugar (cinnamic, caffeic, ferulic, methylcumaric, etc.) are almost always in the trans form and rarely in the cis form; apiose, arabinose, galactose and glucose sugars always have a β-D glycosidic bond, whereas ramnose and xylose an α-D glycosidic bond.

On the basis of the number and type of sugars bound, phenylpropanoid glycosides are divided into monosaccharides, disaccharides and trisaccharides. Monosaccharides have a glucopyranose molecule between the phenylethanol chain and the acid bound with an ester bond; disaccharide glucosides derive from monosaccharides and are classified according to the sugar bound to the glucose.

The most widely represented group in nature, however, remains that of trisaccharides, which contain ramnose as second glucidic unit, to which a third is bound, generally glucose, xylose, apiose, galactose, lixose or ramnose. Aromatic acids most frequently bound to C-4 of glucose are caffeic, ferulic, cinnamic acids.

The authors have now found that the prevention and/or treatment activity of hair loss and/or thinning and stimulation of the hair bulb mainly relates to the presence of phenylpropanoid glucosides.

Typically, their chemical structure is characterized by the presence of a derivative of cinnamic acid and a derivative of 2,4-dihydroxy-phenylethanol, both bound to a same molecule of D-glucopyranose, by means of an ester bond and a glycosidic bond, respectively. Other saccharide molecules such as glucose, ramnose, xylose and apiose, can be bound individually and in different positions in sequence with the glucose molecule which acts as a bridge between the two aromatic structures.

According to an aspect of the present invention, the use of phenylpropanoid glucosides is provided for the production of a composition or preparation for preventing or treating hair loss or stimulating hair growth. Preferred phenylpropanoid glucosides are Phenylpropanoid A and Phenylpropanoid B having the following formula:

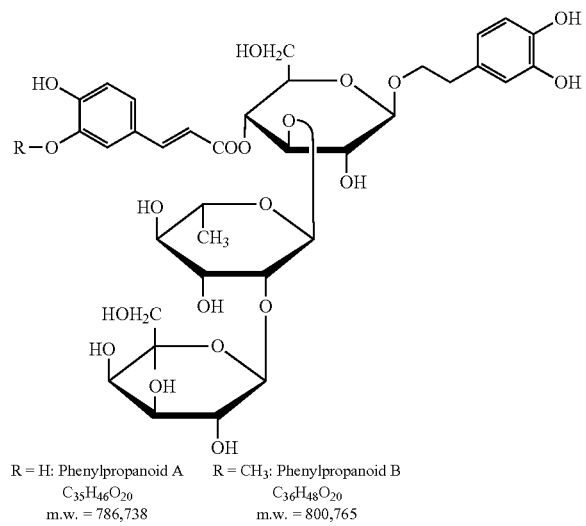

R = H: Phenylpropanoid A  R = CH$_3$: Phenylpropanoid B
C$_{35}$H$_{46}$O$_{20}$ C$_{36}$H$_{48}$O$_{20}$
m.w. = 786,738 m.w. = 800,765

Phenylpropanoid A defined as Teupolioside β-(3,4-dihydroxyphenyl)ethyl-O-α-L-ramnopyranosyl (1″-3′)-O-β D-galactopyranosyl (1‴-2″)-β-D-(4′-O-caffeoyl)-glucopyranoside, is particularly preferred.

The phenylpropanoid glucosides can be advantageously obtained from an extract of *Ajuga reptans*.

According to another aspect of the invention, a method is provided for the preparation of a vegetal homogenate or extract from an *Ajuga reptans* plant comprising the vegetal culture of cellular lines coming from a tissue explant of said plant.

According to an embodiment, in order to obtain an extract from *Ajuga reptans*, the callous tissue is grown preventing its differentiation. Cultures are obtained which do not re-acquire or reproduce the typical morphology of the plant, but which maintain the potentiality of producing typical secondary metabolites. By varying the composition of culture mediums, it is possible to select cellular lines with different biochemical and metabolic characteristics. The preservation of embryonic characteristics mainly occurs by the action of hormonal substances such as, for example, auxine and cytokines, also called "growth factors", produced in nature by the plants themselves and capable of maintaining the meristematic activity in life. The cultures also typically require a suitable culture medium which take into account the metabolic necessity of the cells, the loss of photosynthetic capacity and suitable environmental conditions. The generation and selection phase of the vegetal cellular lines also depend on the number of explants effected as, in spite of the sterilization procedure, most of the explants, from 70% to 80%, are polluted and conveniently disposed of. After an adequate period of time, typically equal to about 21 days of preservation in the dark at a temperature ranging from 20 to 35° C., preferably 28° C., the production of undifferentiated callous tissue can be observed from some explant fragments. In order to obtain multiplication of the callus, the tissue is transferred to a vaster surface with a new medium, and typically, after a further 7-20 days, preferably after 14 days, the parts of the callus which have developed are transferred (subcultivated) on fresh medium.

Once lines have been obtained in rapid growth, but still extremely variable from the point of view of both morphology and productivity, it is possible to select different cellular lines but with uniform characteristics with time.

For the production of reasonable quantities of metabolites, it is then necessary to transfer the lines selected to liquid medium, i.e. proceed with cultures in suspension contained in laboratory flasks or in suspensions cultures.

Lines selected for their proliferative and metabolic characteristics can therefore be cultivated in suspension in flasks or in bioreactors, guaranteeing the production of quantities adequate for the experimental study of the products.

For the quantitative production on an industrial scale of individualized vegetal active principles, a technique has been developed which envisages the preparation of large-volume bioreactors in which the cellular cultures selected are suspended in liquid medium and given the possibility of producing high quantities of biomass.

A schematization of the extraction process according to an embodiment of the present invention is illustrated in FIG. 1 enclosed.

With reference to FIG. 1, a flow scheme is illustrated of an extraction embodiment which comprises the preliminary explant phases of suitable vegetal tissue, preferably consisting of callous tissue 1, sterilization and culture 2 of the vegetal cells from explanted callous tissue, selection in solid medium 3, increase of biomass in liquid 4, insemination in a bioreactor 5, homogenization of the cellular suspension 6, filtration of the suspension and chromatography of the filtrate 7, production of the raw extract 8, purification of the vegetal main principle 9.

This extraction method allows the preparation of differentiated products with specific characteristics of purity and titratability.

In particular, said method allows the identification of:
I) the homogenate of *Ajuga reptans* or the homogenate of whole cells which keeps the trophic principles and nutrients of the vegetal cell intact;
II) the extract purified in Phenylpropanoid or a characterized mixture of phenylpropanoids with a titer higher than 60%;
III) pure Phenylpropanoids essentially corresponding to Phenylpropanoid A with a titer higher than 90%.

According to a first embodiment, the homogenate of *Ajuga reptans* is obtained from cellular cultures of *Ajuga reptans* cultivated according to the method described above. The total homogenate obtained of the whole cells comprises a composition rich in simple and complex nutrients, characteristic active principles, trophic factors and water. The homogenate of *Ajuga reptans* is typically based on different active species, comprising polysaccharides, proteins, lipids and water. The active principles which mainly characterize the activity profile of the homogenate of *Ajuga reptans* mainly comprise non-enzymatic antioxidants such as phenylpropanoids, but also glycoproteins and the polysaccharide fraction and water.

The presence of phenylpropanoids exerts anti-inflammatory effects and inhibition on the 5α-reductase enzyme, on the skin.

When phenylpropanoids are present in association with the other active principles mentioned above, a strong hydration effect is also verified, accompanied by an activity of the trophic type, capable of activating the reparative properties of the skin. As the skin is an organ which is particularly sensitive to the oxidative stress induced by noxae endogen and hexogen, the homogenate, rich in substances with an antioxidant activity, exerts a considerable anti-inflammatory activity. The glycoproteins present in the homogenate are capable of coordinating a vast number of molecules of water through their glycosilated portions, and this capacity strictly depends on the role played in the proliferative phase of the vegetal cell itself; there is in fact an improvement in the elasticity of the cellular walls, favouring the distention and cellular growth and this can have functional implications also on a cutaneous level above all in those situations in which it is useful to stimulate tissular reparation processes. Due to their chemical nature and biological role, the polysaccharides present in the homogenate are capable of coordinating the water, by miming the effect of hyaluronic acid, dermatansulfate and chondroitinsulfate characteristically contained in animal skin. The polysaccharide fraction also contains glucanes to which immunostimulating properties are ascribed.

According to an embodiment, the extract purified in phenylpropanoid is produced by a progressively selected cellular line of *Ajuga reptans*. The cells coming from the cellular culture are mechanically crushed and filtered. The filtrate is conveniently extracted for the phenylpropanoids on affinity resin and eluted with a hydro-alcohol solution.

According to a preferred embodiment, the glucosides of phenylpropanoids are extracted from tissues of *Ajuga reptans*.

It has been verified that the homogenate or vegetal extract from *Ajuga reptans* exerts a synergic regulation effect of the trophism of some epithelial structures, with particular reference to the sebaceous glands and hair follicles. In particular, the administration of the extract or homogenate in the form of a composition determines a reduction in the secretion of sebum with beneficial effects on acne and seborrhea and a regulation of the physiological growth of hair and hairs, with a favourable result on androgenetic alopecia, telogenic defluvium, hypertricosis and hirsutism.

The extract or homogenate from *Ajuga reptans* used within the scope of the invention can be typically alcoholic, hydroalcoholic, glyceric, acetonic, the use of hydro-alcoholic or acetonic being preferred.

It has in fact been observed that with the extraction, it is possible to obtain an end-product rich in phenylpropanoids and in vegetal substances active in selectively inhibiting the 5α-reductase enzyme, highly expressed at the level of the follicles.

The composition of the invention can be used either in topic or systemic applications and has proved to be effective in preventing and/or treating affections caused by an excessive production of sebum such as acne, seborrhea, furunculosis, and affections caused by the activity of 5α-reductase, such as androgenetic alopecia, telogenic defluvium, hair thinning and also hypertricosis and/or hirsutism.

The composition of the invention is particularly suitable in the treatment of androgenetic alopecia.

The compositions for topic application of the invention can be in liquid form such as lotions and solutions, and also in solid form, such as gels, creams, ointments, pomades, masks, transdermal plasters with a prolonged release.

The compositions for local application of the invention can conveniently comprise additives commonly used in cosmetic or pharmaceutical preparations for local use, such as preservatives, bacterial agents, stabilizers, emulsifying agents, buffers, dyes and other excipients commonly used in cosmetic/pharmaceutical preparation techniques.

In the case of a liquid formulation, the synergic active principles of the invention can be conveniently dissolved in a cosmetically/pharmaceutically acceptable liquid vehicle such as water, alcohol, hydro-alcohol, glyceric solution and other types suitable for local application.

For illustrative purposes, the compositions of the invention in liquid form are prepared by dissolving the hydrosoluble vegetal extracted fractions in water and the remaining fractions in alcohol, subsequently joining the different fractions under stirring. The resulting mixture can then be buffered to reach a pH range conveniently selected from 5 to 7 so as to be compatible with the pH of the skin, and is then filtered and packaged in suitable containers such as small bottles or phials.

The composition for local use of the invention is used for applications, in an effective quantity, directly on the affected body region to be treated.

In the treatment of androgenetic alopecia, for example, a lotion based on the active principles of the invention is applied directly on the scalp, once or twice a day, conveniently for cycles lasting 2-3 months alternating with rest periods.

Similarly, a composition in the form of a cream can be applied once or twice a day on the face of a subject affected by seborrhea or acne, for example, until the remission of the affection.

In the case of a solid or semi-solid formulation, the synergic active principles of the invention are dispersed in cosmetically/pharmaceutically acceptable vehicles, commonly used for local application.

The application of the composition of the invention in the form of a cream leads to a reduction in the secretion of sebum on the part of the sebaceous glands which is visible after a few days of treatment as a reduction in the greasiness of the body surface treated.

The compositions of the invention for oral use can be applied in the form of tablets, capsules, liquid solutions and in forms for the controlled release of the active principles.

The preparation for oral administration of the invention is obtained by means of the normal preparation techniques of dietetic and/or pharmaceutical products, by adding one or more physiologically acceptable vehicle to the synergic active principles. Physiologically acceptable vehicles are therefore used in a mixture with suitable preservatives, stabilizers, excipients, carrying and aromatizing agents.

In the composition of the invention, the synergic active principles of the invention are present in varying quantities, typically ranging from 0.001% by weight to 10% by weight, more preferably from 0.1 to 5% by weight.

According to another aspect of the invention, a cosmetic treatment method is provided which comprises the local application, at the level of the scalp or face, of an effective quantity of a composition described above.

The following examples are provided for purely illustrative purposes of the present invention and should in no way be considered as limiting the protection scope, as indicated in the enclosed claims.

EXAMPLE 1

Integrator in tablet form suitable for reducing damage from oxidative stress due to solar rays at the level of the keratin structures:

Each tablet contains:

| | |
|---|---:|
| Calcium pantotenate | 9 mg |
| d-Biotin | 0.150 mg |
| *Ajuga reptans* | 5 mg |
| Beta carotene | 7.2 mg |
| Ubidecarenone | 10.0 mg |
| Zinc (as chelated amino acid) | 7.5 mg |
| Copper (as chelated amino acid) | 1.20 mg |
| Folic acid | 0.30 mg |
| Microcrystalline cellulose | 17.0 mg |
| Bibasic calcium phosphate bihydrate | 62.0 mg |
| Hydroxypropylmethylcellulose | 80.0 mg |
| Magnesium stearate | 7.90 mg |
| Silicon bioxide | 1.70 mg |

EXAMPLE 2

Dietetic integrator in tablet form based on *Ajuga, Boehmeria nivea* and a sulfur donor (methionine):

Each tablet contains:

| | |
|---|---:|
| Methionine | 300 mg |
| Calcium pantotenate | 9 mg |
| d-Biotin | 0.150 mg |
| *Ajuga reptans* | 5 mg |
| Zinc (as chelated amino acid) | 7.5 mg |
| Copper (as chelated amino acid) | 1.20 mg |
| Manganese (as chelated amino acid) | 2.25 mg |
| Vitamin B6 | 3.0 mg |
| Folic acid | 0.30 mg |
| Microcrystalline cellulose | 17.0 mg |
| Bibasic calcium phosphate bihydrate | 62.0 mg |
| Hydroxypropylmethylcellulose | 80.0 mg |
| Magnesium stearate | 7.90 mg |
| Silicon bioxide | 1.70 mg |

EXAMPLE 3

Integrator in tablet form based on Phenylpropanoids from *Ajuga reptans*, with an anti-aging activity.

Each tablet contains:

| | |
|---|---:|
| Calcium pantotenate | 9 mg |
| d-Biotin | 0.150 mg |
| Phenylpropanoid A + B | 2.5 mg |
| Zinc (as chelated amino acid) | 7.5 mg |
| Copper (as chelated amino acid) | 1.20 mg |
| Folic acid | 0.30 mg |
| Microcrystalline cellulose | 17.0 mg |
| Bibasic calcium phosphate bihydrate | 62.0 mg |
| Hydroxypropylmethylcellulose | 80.0 mg |
| Magnesium stearate | 7.90 mg |
| Silicon bioxide | 1.70 mg |

EXAMPLE 4

Integrator particularly suitable for androgenetic alopecia and telogenic defluvium in women close to or during menopause:

Each tablet contains:

| | |
|---|---:|
| Calcium pantotenate | 9 mg |
| d-Biotin | 0.150 mg |
| Soya Isoflavones (genistein and daidzein) | 40 mg |
| *Boehmeria nipononivea* | 100 mg |
| *Ajuga* | 2.5 mg |
| Resveratrol | 0.05 mg |
| Zinc (as chelated amino acid) | 7.5 mg |
| Copper (as chelated amino acid) | 1.20 mg |
| Folic acid | 0.30 mg |
| Microcrystalline cellulose | 17.0 mg |
| Bibasic calcium phosphate bihydrate | 62.0 mg |
| Hydroxypropylmethylcellulose | 80.0 mg |
| Magnesium stearate | 7.90 mg |
| Silicon bioxide | 1.70 mg |

EXAMPLE 5

Integrator in tablet form suitable for the prevention of male and female androgenetic alopecia:

Each tablet contains:

| | |
|---|---:|
| Calcium pantotenate | 9 mg |
| d-Biotin | 0.150 mg |
| *Boehmeria nipononivea* | 200 mg |
| *Ajuga reptans* | 5 mg |
| Quercetin | 0.90 mg |
| Taurine | 200 mg |
| Zinc (as chelated amino acid) | 7.5 mg |
| Copper (as chelated amino acid) | 1.20 mg |
| Microcrystalline cellulose | 90.0 mg |
| Bibasic calcium phosphate bihydrate | 80.0 mg |
| Hydroxypropylmethylcellulose | 52.5 mg |
| Magnesium stearate | 7.90 mg |
| Silicon bioxide | 1.70 mg |

EXAMPLE 6

Dermatological cream for reducing damage of hair and skin bulbs from exposure to UV rays The composition comprises:

| | |
|---|---:|
| Calcium pantotenate | 9 mg |
| d-Biotin | 0.150 mg |
| *Ajuga reptans* | 20.0 mg |
| Macrogol cetosteraryl ether | 5.0 g |
| Isopropyl myristate | 4.0 g |
| Propylene glycol | 3.0 g |
| Glycerin | 3.0 g |
| White Vaseline | 11.0 g |
| Cetostearylic alcohol | 9.0 g |
| Methyl paraoxybenzoate | 0.2 g |
| Propyl paraoxybenzoate | 0.02 g |
| EDTA tetrasodic | 0.1 g |
| Water | complement to 100 g |

EXAMPLE 7

Lotion useful for male and female telogenic defluvium for topic use:

| | |
|---|---|
| Calcium pantotenate | 30.0 mg |
| d-Biotin | 0.30 mg |
| *Ajuga reptans* | 5.0 mg |
| Beta glucane | 0.50 mg |
| Fitotocotrienols | 20 mg |
| Grapefruit seed extract | 30 mg |
| Disodium Edta | 3.0 mg |
| PEG-40 Hydrogenated castor oil | 30 mg |
| Perfume | 6.0 mg |
| Citric acid | 1.5 mg |
| Type C denatured alcohol | 1.5 g |
| Water | complement to 10 g |

EXAMPLE 8

Composition for topic use based on *Ajuga* particularly suitable for anti-inflammatory action in the cases of Acne and seborrhea:

| | |
|---|---|
| Calcium pantotenate | 30.0 mg |
| d-Biotin | 0.30 mg |
| *Ajuga reptans* | 5.0 mg |
| Cetearet-22, Palmeth-2 | 5.0 g |
| Caprylic/capric triglyceride | 5.0 g |
| White Vaseline | 2.0 g |
| Octyldodecyl myristate | 3.0 g |
| Cetylstearylic alcohol | 2.0 g |
| Perfume | 0.20 g |
| Conc. Tocoferol | 0.05 g |
| 2-phenoxyethanol and parabens | 0.6 g |
| Cyclomethicone | 0.05 g |
| Propylene glycol | 3.45 g |
| Glycerin | 3.2 g |
| Alkyl Acrylates crosspolymer | 0.60 g |
| EDTA tetrasodic | 0.10 g |
| Amino methylpropanol | 0.45 g |
| Water | complement to 100 g |

EXAMPLE 9

Composition for the local application in the form of an extemporaneous mask useful in cases of hypertricosis.

| | |
|---|---|
| *Ajuga reptans* | 20.0 mg |
| *Boehmeria nipononivea* | 8 g |
| Spermidine trihydrochloride | 2.0 mg |
| Calcium pantotenate | 30.0 mg |
| d-Biotin | 0.30 mg |
| Isagel FM alginate | complement to 100 g |

EXAMPLE 10

Sun gel for topic use based on *Ajuga reptans:*

| | |
|---|---|
| *Ajuga* | 20.0 mg |
| Calcium pantotenate | 30.0 mg |
| Denatured alcohol | 20.0 g |
| EDTA disodic | 0.05 g |
| Glycerin | 2.0 g |
| Betaine | 0.5 g |
| Aristoflex | 1.2 g |
| Parsol MCX | 5.0 g |
| Parsol 1789 | 3.0 g |
| Eusolex | 3.0 g |
| *Butyrospermum parkii* | 2.0 |
| Trimethylsilylamodimeticone | 0.5 |
| *Rosmarinum officinalis* | 0.1 g |
| Conc. Carotene | 0.01 g |
| Cyclopentaxyloxane | 3.00% |
| Water | complement to 100 g |

EXAMPLE 11

Dermatological cream
100 g of cream contain:

| | |
|---|---|
| *Ajuga reptans* | 0.1 g |
| PEG 400 | 20.0 g |
| PEG 1500 | 15.0 g |
| PEG 4000 | 45.0 g |
| Cetostearylic alcohol | 2.0 g |
| 2-Phenoxyethanol | 0.90 g |
| Glycerin | 4.0 g |
| Liquid paraffin | 2.0 g |
| Demineralized water | complement to 100 g |

EXAMPLE 12

Hydroalcoholic lotion with *Ajuga reptans* and Taurine
One 5 ml dose contains:

| | |
|---|---|
| EDTA disodic | 3.0 mg |
| Taurine | 100.0 mg |
| *Ajuga reptans* | 5.0 mg |
| Alcohol 95% | 750.0 mg |
| Demineralized water | complement to 5.0 ml |

EXAMPLE 13

Hydroalcoholic lotion with *Ajuga reptans*
One 5 ml dose contains:

| | |
|---|---|
| EDTA disodic | 3.0 mg |
| Phenlypropanoid A + B | 2.5 mg |
| Alcohol 95% | 750.0 mg |
| Demineralized water | complement to 5.0 ml |

EXAMPLE 14

Physiological gel for topic use with *Ajuga reptans*.
100 g of gel contain:

| | |
|---|---|
| Hydroxyethylcellulose | 0.5 g |
| *Ajuga reptans* | 0.1 g |
| Sodium Chloride | 0.9 g |

-continued

| Propylene glycol | 3.0 g |
| Imidazolidinyl urea | 0.50 g |
| Methylchloroisothiazolinone | 0.0009 g |
| Methylisothiazolinone | 0.0003 g |
| EDTA disodic | 0.05 g |
| Demineralized water | complement to 100 g |

EXAMPLE 15

Gel for ionophoresis
100 of gel contain:

| Hydroxyethylcellulose | 1.5 g |
| *Ajuga reptans* | 0.1 g |
| Potassium Choride | 4.5 g |
| Propylene glycol | 1.0 g |
| Imidazolidinyl urea | 0.40 g |
| Methylchloroisothiazolinone | 0.0009 g |
| Methylisothiazolinone | 0.0003 g |
| EDTA disodic | 0.05 g |
| Demineralized water | complement to 100 g |

EXAMPLE 16

The percentage composition was analyzed of homogenate of *Ajuga reptans* obtained from cellular cultures from callous tissue of *Ajuga reptans* cultivated in bioreactors in which the cells are suspended in liquid medium for vegetal cellular cultivations.
Composition

| Fraction | Content (w/w %) |
| --- | --- |
| Polysaccharides | 6.89 |
| Phenyl propanoid complexes | 0.15 |
| Proteins of which | 1.71 |
| Glycoproteins | Not less than 20%, equal to 0.34% of the total |
| Lipids | 0.76 |
| Ash | 0.31 |
| Water | 90.19 |
| pH | 4.00 |

The water present in the homogenate is strictly coordinated to the glycosylation and polysaccharide molecules. The lipidic fraction extracted from the lyophilized product has an interesting composition which is indicated in the following table and is mainly characterized by beta-sitosterol. The acid fraction mainly consists of palmitic acid, oleic acid and linoleic acid.

| Sterol composition | 97.85 g/100 g |
| --- | --- |
| Cholesterol | 4.05 g/100 g |
| 24-Methylenecholesterol | 2.92 g/100 g |
| Campesterol | 1.52 g/100 g |
| Campestanol | 1.00 g/100 g |
| Stigmasterol | 0.68 g/100 g |
| Delta-7-campesterol | 17.41 g/100 g |
| Beta-sitosterol | 70.52 g/100 g |
| Sitostanol | 1.67 g/100 g |
| Delta-5,24-Stigmastadienol | 0.20 g/100 g |
| Delta-7-Avenasterol | 0.81 g/100 g |

| Acidic composition | w/w |
| --- | --- |
| Caprinic acid | 1.29 |
| Lauric acid | 0.34 |
| Myristic acid | 0.61 |
| Pentadecanoic acid | 0.36 |
| Palmitic acid | 21.68 |
| Palmitoleic acid | 0.47 |
| Stearic acid | 4.38 |
| Oleic acid | 42.78 |
| Linoleic acid | 17.62 |
| Linolenic acid | 1.98 |
| Behenic acid | 0.41 |
| Lignocetic acid | 0.74 |

Determination of the humidity (70° C.) of a sample of homogenate of *Ajuga reptans* as such and neutralized with arginine 10%.

The determination of the humidity was effected in an oven (model Memmert TV 500) at a temperature of 70° C. Approximately 10 g of *Ajuga reptans* extract in a calibrated glass beaker were weighed with an analytical scale (Gibertini model E42). The beaker was then hermetically closed with aluminum film and subsequently weighed. It was then placed in an oven for 48 hours at a temperature of 70° C. After the pre-established time, the beaker hermetically closed with aluminum film was reweighed.

| Type of Extract | Humidity at 70° C. (%) |
| --- | --- |
| Extract of *Ajuga reptans* as such | 70.24 |
| Extract of *Ajuga reptans* neutralized at pH 5.57 | 64.45 |

The neutralization of the *Ajuga reptans* extract was obtained by the progressive addition of a solution of Arginine (100 (w/w) up to a pH value within the range of 5.50-5.60.

EXAMPLE 17

Formulation with *Ajuga reptans* Homogenate
A product based on monophasic systems such as gels and biphasic systems such as emulsions can be easily produced as the *Ajuga reptans* extract can be easily included in both types of formulation, also up to 25% w/w. The formulation with the *Ajuga reptans* homogenate, on a laboratory test level, is in fact easy to handle and does not require particular mechanical expedients, unless at high concentrations (higher than 40%).
Dermatological Tolerability
The patch test effected on healthy volunteers confirmed that the product does not have problems relating to skin tolerability

EXAMPLE 18

A study was carried out to determine in-vivo the inhibitory activity of 5α-reductase on the part of a total extract deriving from a cellular culture of *Ajuga reptans*.
The study was effected by determining the haematic levels of DHT (5α-dihydrotestosterone) on rats after administration of the extract being studied. These levels were compared with both basal levels and with those obtained after administration of Finasteride, which currently represents the most active inhibitor of the 5α-reductase enzyme, responsible for the transformation of testosterone in its most active form, DHT.

Materials and Methods

For the in-vivo study of the inhibition of 5α-reductase, Sprague-Dawley adult male rats were used (Charles River Italia) having a body weight of 200-250 g.

The animals were stalled under standard conditions: at a temperature of 22/23° C., with 65% relative humidity, exposing them to illumination cycles of 12 h light/12 h darkness.

A standard diet in the form of pellets (standard diet, Charles River) was administered to the rats, with water ad libitum The experimentation was carried out according to protocols authorized by the Committee for the Care and Use of Animals of the Università degli Studi of Milan. Tests were carried out on the rats, effected from the retro-orbital plexus, immediately before the pharmalogical treatment ($t_0$) and subsequently at a distance of 3, 6 and 8 hours after administration.

The administration of the substances being studied was effected orally.

In correspondence with each test on the animals treated, tests were also effected on non-treated animals to determine the basal analyte level. Both testosterone and DHT are in fact characterized by a significant circadian fluctuation.

The plasma obtained from the whole blood treated with EDTA after centrifugation was preserved at −20° C. until dosage.

The plasmatic concentrations of DHT (dihydrotestosterone) were determined with a commercial kit (DSL, Chematil, Angri, SA) after extraction of the samples.

All the samples of an experimental set were dosed together to reduce the inter-analytic variability.

Results

The results are indicated in the following table

TABLE 1

Seric concentrations of DHT (pg/ml) after in vivo administration in rats

| Basal | | | Finasteride 1 mg | | | Finasteride 5 mg | | | Ajuga 5 mg | | |
|---|---|---|---|---|---|---|---|---|---|---|---|
| | | | 3 hrs | 6 hrs | 8 hrs | 3 hrs | 6 hrs | 8 hrs | 3 hrs | 6 hrs | 8 hrs |
| 345.4 | 397.1 | 720.8 | 298.1 | 404.1 | 706.7 | 217.1 | 103.6 | 201.6 | 222.4 | 80.4 | 78.5 |
| 266.4 | 162.7 | 350.4 | 505.3 | 565.0 | 140.1 | 618.6 | 54.4 | 108.8 | 101.1 | 54.9 | 59.3 |
| 474.2 | 273.0 | 824.5 | 300.0 | 379.6 | 503.9 | 151.2 | 60.7 | 745.4 | 177.8 | 68.8 | 62.5 |
| 290.8 | 195.6 | 615.7 | 569.6 | 592.1 | 530.1 | 641.0 | 49.7 | 576.6 | 146.4 | 120.7 | 125.0 |
| 89.8 | 138.1 | 62.5 | 404.6 | 148.5 | 173.1 | 924.2 | 128.3 | 250.9 | 85.2 | 58.7 | 62.5 |
| 191.8 | 434.4 | 114.5 | 530.0 | 420.1 | 110.0 | 569.4 | 176.9 | 300.1 | 141.6 | 117.4 | 49.1 |
| 337.1 | 673.6 | 46.4 | | | | | 81.2 | | | | |
| 88.6 | 345.0 | 905.3 | | | | | 205.2 | | | | |
| 102.7 | 581.6 | 63.7 | | | | | | | | | |
| 62.5 | 867.6 | 164.9 | | | | | | | | | |
| 91.9 | 506.4 | 1165.9 | | | | | | | | | |
| 171.5 | 206.2 | 389.5 | | | | | | | | | |
| 124.0 | 152.0 | 100.5 | | | | | | | | | |
| n = 39 | | | 6 | 6 | 6 | 6 | 8 | 6 | 6 | 6 | 6 |
| average 335.7 | | | 434.6 | 418.2 | 360.6 | 520.2 | 107.5 | 363.9 | 145.7 | 83.5 | 72.8 |
| Stand. error 44.4 | | | 48.3 | 64.9 | 102.6 | 118.0 | 20.6 | 99.8 | 20.5 | 11.8 | 11.1 |

Figure 2:
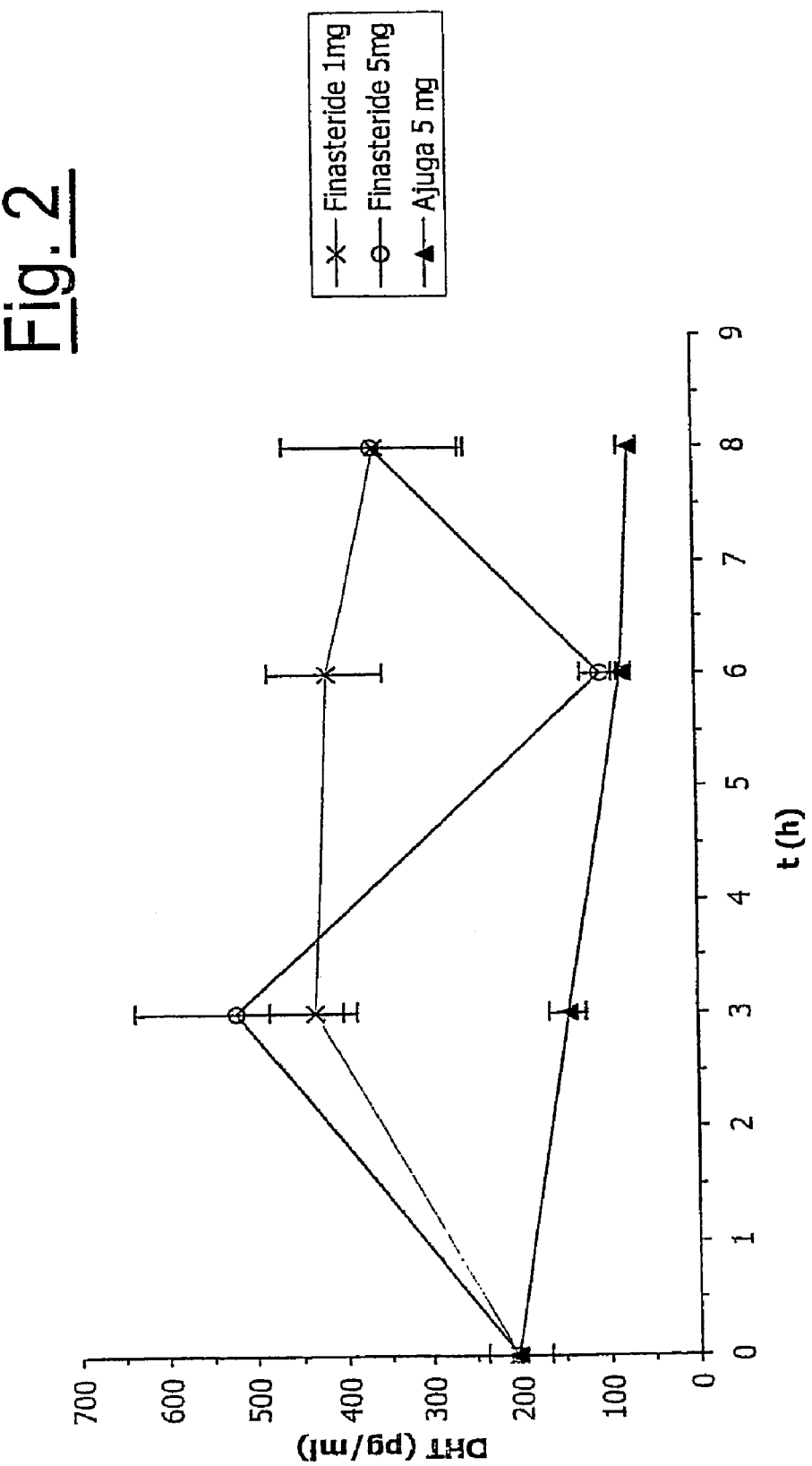
FIG. 2 is graph of the concentration of DHT vs finasteride and the *Ajuga* extract.

The graphic representation of the trend of the concentration of DHT after administration is indicated in FIG. 2 enclosed.

The reductions in the concentrations of DHT are statistically significant.

*Ajuga* 6 h vs. basal p<0.03;
*Ajuga* 8 h vs. basal p<0.02.

As can be seen from the data and graph, the concentration of DHT is already reduced after the first three hours, to reach, at 6 hours, the same levels as that obtained with the administration of 5 mg of finasteride. The total extract of *Ajuga reptans* therefore showed an inhibiting capacity of 5α-reductase comparable to that of finasteride, but more rapid and longer lasting as with finasteride, 8 hours after treatment, the DHT rises returning to the basal levels.

The invention claimed is:

1. A composition consisting essentially of purified explant culture of *Ajuga reptans* phenylpropanoids comprising a mixture of phenylpropanoids with a titer equal to or higher than 50% by weight of glucoside.

2. The composition of claim 1, wherein said phenylpropanoids are phenylpropanoid A with a titer equal to or higher than 90%.

3. A method of treating acne or hair loss in a subject in need thereof consisting essentially of administering therapeutically effective amounts of the composition of claim 1 to the subject.

* * * * *